US011123512B2

(12) United States Patent
Allum

(10) Patent No.: US 11,123,512 B2
(45) Date of Patent: Sep. 21, 2021

(54) CONNECTION OF A SPONTANEOUS DELIVERY DEVICE TO A CONCENTRATOR

(71) Applicant: SILVERBOW DEVELOPMENT, LLC, San Ramon, CA (US)

(72) Inventor: Todd Allum, Livermore, CA (US)

(73) Assignee: INOGEN, INC., Goleta, CA (US)

(*) Notice: Subject to any disclaimer, the term of this patent is extended or adjusted under 35 U.S.C. 154(b) by 875 days.

(21) Appl. No.: 15/299,434

(22) Filed: Oct. 20, 2016

(65) Prior Publication Data

US 2017/0113013 A1    Apr. 27, 2017

Related U.S. Application Data

(60) Provisional application No. 62/245,966, filed on Oct. 23, 2015.

(51) Int. Cl.
*A61M 16/10* (2006.01)
*B01D 53/053* (2006.01)
(Continued)

(52) U.S. Cl.
CPC ........ *A61M 16/101* (2014.02); *A61M 16/125* (2014.02); *B01D 51/00* (2013.01);
(Continued)

(58) Field of Classification Search
CPC .............. A61M 16/101; A61M 16/125; A61M 2016/0039; A61M 16/105;
(Continued)

(56) References Cited

U.S. PATENT DOCUMENTS 7,294,170 B2    11/2007  Richey, II et al.
7,445,663 B1 *  11/2008  Hunter ................ B01D 53/047
                                                      128/204.21
(Continued)

FOREIGN PATENT DOCUMENTS

EP          2 063 946 A1    6/2009
WO      2008/036159 A1    3/2008
WO      2013/038319 A1    3/2013

OTHER PUBLICATIONS

International Search Report for International Application No. PCT/US2016/058279 dated Jan. 10, 2017.
(Continued)

*Primary Examiner* — Margaret M Luarca
(74) *Attorney, Agent, or Firm* — Artegis Law Group, LLP

(57) ABSTRACT

One embodiment of the present invention sets forth a technique for operating an oxygen concentrator. The technique includes measuring a product gas within an oxygen concentrator to produce a product gas measurement, and determining that an output of the oxygen concentrator is fluidly connected to a respiratory ventilation device based on the product gas measurement. The technique further includes, in response to determining that the oxygen concentrator is fluidly connected to the respiratory ventilation device, determining that the output of the oxygen concentrator does not meet a supply gas requirement of the respiratory ventilation device and, in response to determining that the output of the oxygen concentrator does not meet the supply gas requirement, adjusting a control output in the oxygen concentrator to modify operation of the oxygen concentrator.

23 Claims, 5 Drawing Sheets

(51) Int. Cl.
  *B01D 53/04* (2006.01)
  *A61M 16/12* (2006.01)
  *B01D 51/00* (2006.01)
  *B01D 53/047* (2006.01)
  *B01D 53/54* (2006.01)
  *A61M 16/00* (2006.01)
  *A61M 16/20* (2006.01)

(52) U.S. Cl.
  CPC ....... *B01D 53/0407* (2013.01); *B01D 53/047* (2013.01); *B01D 53/0423* (2013.01); *B01D 53/0446* (2013.01); *B01D 53/0454* (2013.01); *B01D 53/0473* (2013.01); *B01D 53/0476* (2013.01); *B01D 53/053* (2013.01); *B01D 53/54* (2013.01); *A61M 16/0063* (2014.02); *A61M 16/105* (2013.01); *A61M 16/201* (2014.02); *A61M 2016/003* (2013.01); *A61M 2016/0027* (2013.01); *A61M 2016/0039* (2013.01); *A61M 2016/1025* (2013.01); *A61M 2205/14* (2013.01); *A61M 2205/3334* (2013.01); *A61M 2230/42* (2013.01); *B01D 2253/108* (2013.01); *B01D 2256/12* (2013.01); *B01D 2257/102* (2013.01); *B01D 2259/402* (2013.01); *B01D 2259/4006* (2013.01); *B01D 2259/40009* (2013.01); *B01D 2259/40013* (2013.01); *B01D 2259/40028* (2013.01); *B01D 2259/40035* (2013.01); *B01D 2259/40084* (2013.01); *B01D 2259/4533* (2013.01)

(58) Field of Classification Search
  CPC ........... A61M 2205/14; B01D 53/0423; B01D 53/053; B01D 53/0454; B01D 53/047; B01D 53/0473; B01D 53/0476; B01D 53/0446; B01D 2259/40009; B01D 2259/4533
  See application file for complete search history.

(56) References Cited

U.S. PATENT DOCUMENTS

| | | | |
|---|---|---|---|
| 7,708,802 B1 | 5/2010 | Deane et al. | |
| 7,722,700 B2* | 5/2010 | Sprinkle | B01D 53/047 128/205.12 |
| 2003/0005928 A1 | 1/2003 | Appel et al. | |
| 2006/0124128 A1 | 6/2006 | Deane et al. | |
| 2006/0230929 A1* | 10/2006 | Bliss | B01D 53/0407 95/96 |
| 2007/0039466 A1* | 2/2007 | Nawata | A61M 16/0677 95/96 |
| 2010/0116270 A1* | 5/2010 | Edwards | A61M 16/101 128/201.21 |
| 2011/0247620 A1* | 10/2011 | Armstrong | B01D 53/047 128/204.23 |
| 2012/0055483 A1* | 3/2012 | Wilkinson | B01D 53/053 128/205.27 |
| 2013/0025591 A1 | 1/2013 | Clark et al. | |
| 2015/0059745 A1* | 3/2015 | Barker | A61M 16/0066 128/203.14 |
| 2015/0107585 A1 | 4/2015 | Allum | |
| 2016/0279362 A1* | 9/2016 | DeVries | A61M 16/0883 |

OTHER PUBLICATIONS

Extended European Search Report for Application No. 16858375.5 dated May 29, 2019.

* cited by examiner

CONNECTION OF A SPONTANEOUS DELIVERY DEVICE TO A CONCENTRATOR

CROSS-REFERENCE TO RELATED APPLICATIONS

This application claims benefit of U.S. provisional application titled, "CONNECTION OF A SPONTANEOUS DELIVERY DEVICE TO A CONCENTRATOR," filed on Oct. 23, 2015 and having Ser. No. 62/245,966. The subject matter of this related application is hereby incorporated herein by reference.

BACKGROUND OF THE INVENTION

Field of the Invention

The present invention relates generally to medical devices and, more specifically, to the connection of a spontaneous delivery device to a concentrator.

Description of the Related Art

Oxygen therapy is the standard of care for many patients with lung diseases in the early to mid-stages. In particular, individuals with Chronic Obstructive Pulmonary Disease (COPD), the third leading cause of death in the United States, are prescribed with oxygen therapy to increase blood oxygen saturation. In many cases, patients with COPD can also benefit from improved ventilation of the lungs to help evacuate elevated levels of carbon dioxide. However, such patients are generally not prescribed ventilation therapy until hospitalized or in the late stages of the disease, due to the high cost and large size of traditional mechanical ventilators. While oxygen therapy, ventilation therapy and ventilation with oxygen therapy have all proven to be beneficial therapies for patients with COPD (with increasing benefit, respectfully), oxygen concentrators are generally not well-suited for direct coupling with mechanical ventilators for several reasons.

First, ventilators generally require a gas source that can provide a spontaneous flow rate of more than 100 liters per minute (LPM) to provide adequate ventilation therapy during an inspiratory effort, while a typical oxygen concentrator can deliver a continuous flow rate on the order of only about 1 to 5 LPM, and in some cases up to 10 LPM. Second, connecting the outlet of an oxygen concentrator to a mechanical ventilator requires careful titration of both the concentrator and ventilator settings while utilizing an oxygen sensor to monitor and maintain the required delivered oxygen concentration from the ventilator. Third, oxygen concentrators are typically provided to patients with lung diseases in the early to mid-stages of a disease and not to late-stage patients which typically receive ventilation therapy. Consequently, oxygen concentrators generally do not include the ability to detect patient-related issues or have any means for monitoring patient status, even though such monitoring is highly desirable for seriously ill patients, such as patients receiving ventilation therapy. Instead, oxygen concentrators are typically only configured with monitors and/or alarms related to the operation of the concentrator itself. As a result, oxygen concentrators are generally unable to monitor the status of a patient receiving ventilation and oxygen therapy.

As the foregoing illustrates, what is needed in the art are more effective approaches for interfacing the output of an oxygen concentrator to a mechanical ventilator.

SUMMARY OF THE INVENTION

One embodiment of the present invention sets forth a technique for operating an oxygen concentrator in conjunction with a mechanical ventilator. The technique includes measuring a product gas within an oxygen concentrator to produce a product gas measurement, and determining that an output of the oxygen concentrator is fluidly connected to a respiratory ventilation device based on the product gas measurement. The technique further includes, in response to determining that the oxygen concentrator is fluidly connected to the respiratory ventilation device, determining that the output of the oxygen concentrator does not meet a supply gas requirement of the respiratory ventilation device and, in response to determining that the output of the oxygen concentrator does not meet the supply gas requirement, adjusting a control output in the oxygen concentrator to modify operation of the oxygen concentrator.

At least one advantage of the disclosed techniques is that an oxygen concentrator can be effectively connected to a mechanical ventilator without the performance of the oxygen concentrator being deleteriously affected. In addition, certain aspects of patient status can be monitored noninvasively as part of the normal operation of the oxygen concentrator.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the embodiments of the present invention. However, it will be apparent to one of skill in the art that the embodiments of the present invention may be practiced without one or more of these specific details.

Stationary and portable oxygen concentrators commonly employ a process called pressure swing adsorption (PSA) to increase the oxygen concentration of the incoming ambient air before the air is delivered to a patient. Generally, the delivered oxygen concentration is between 90 and 96%, due to concentrator efficiencies and remaining constituent elements in the air that are not adsorbed in the process. Stationary and most portable oxygen concentrators use the PSA process to deliver a constant flow of oxygen to the patient, typically 1 to 10 LPM, while ultra-portable oxygen concentrators provide even less. For example some ultra-portable oxygen concentrators provide a small pulse of oxygen-enriched gas on the order of about 10 ml upon detection of an inspiratory effort, which is equivalent to a continuous delivery of about 0.5 LPM.

As noted above, the continuous flow rate of oxygen concentrators is generally too low to serve as a gas source for conventional mechanical ventilators: typical ventilators require a source of supply gas that can provide a flow rate of about 100 LPM to provide adequate ventilation therapy during an inhalation. However, ventilators that utilize entrainment technology only require approximately 20 LPM of flow from the ventilator gas source during an inhalation to provide 100 LPM of ventilation support. For a spontaneous intermittent ventilator, the average delivered volume from the gas source (minute volume) is based on the flow during inhalation, the inhalation delivery period and the patient's breath rate. The minute volume typically ranges from 1 to 5 LPM, which is well within the continuous flow rate provided by most stationary oxygen concentrators.

According to embodiments of the invention, the output of an oxygen concentrator, i.e., oxygen-enriched product gas, is fluidly connected to a respiratory ventilation device, thereby facilitating oxygen and ventilation therapy. Furthermore, a controller of the oxygen concentrator is configured to detect the fluid connection to the respiratory ventilation device, and to adjust operation of the oxygen concentrator accordingly. For example, the controller may adjust operation of the oxygen concentrator when the output of the oxygen concentrator does not meet a supply gas requirement of the respiratory ventilation device, such as flow rate or oxygen concentration. In some embodiments, the controller is also configured to monitor one or more aspects of patient status.

Figure 1:
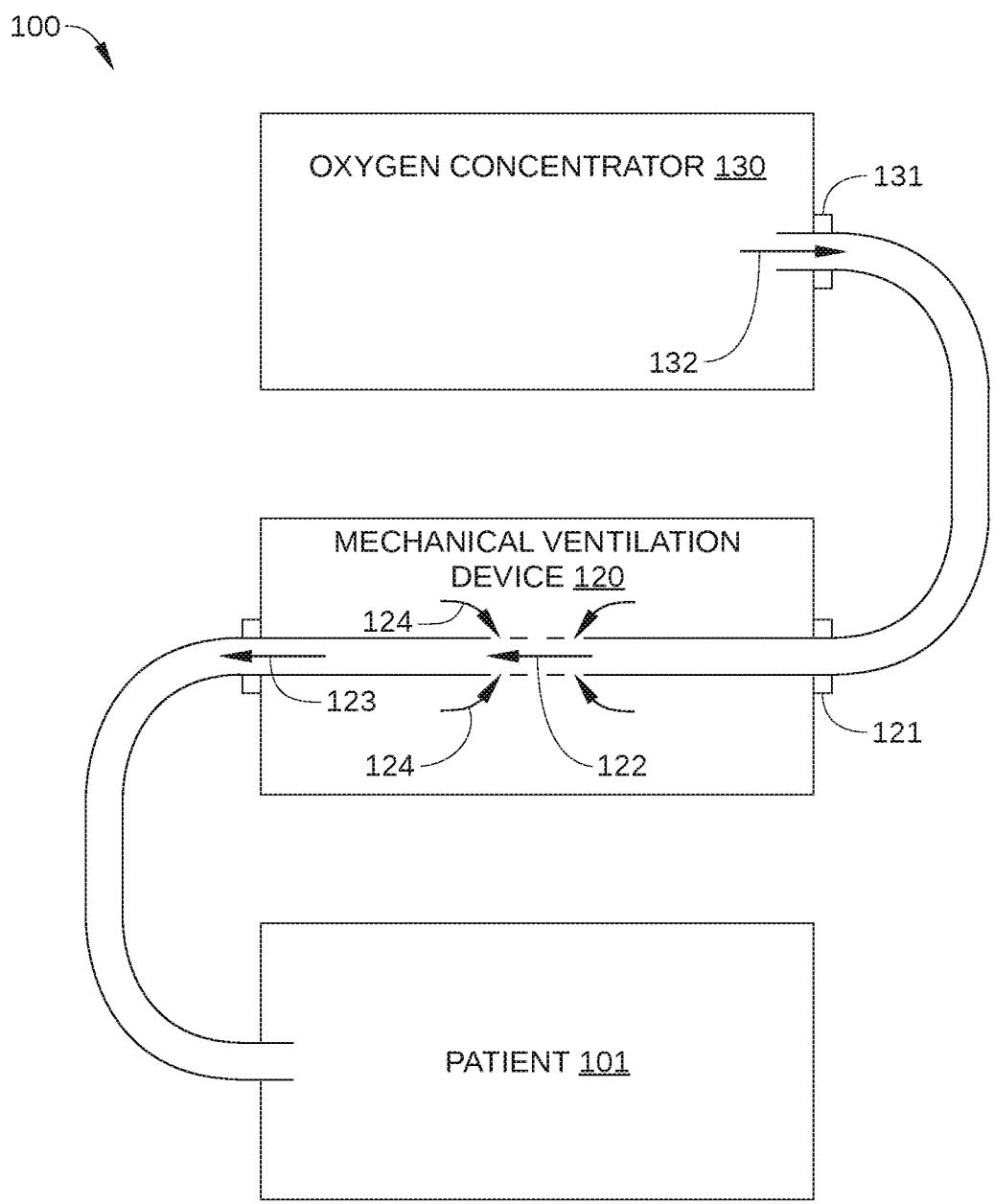
FIG. 1 is a block diagram of an oxygen-ventilation therapy system, according to various embodiments of the present invention.

FIG. 1 is a block diagram of an oxygen-ventilation therapy system 100, according to various embodiments of the present invention. Oxygen-ventilation therapy system 100 is configured to simultaneously provide both oxygen therapy and ventilation therapy to a patient 101, and includes a respiratory ventilation device 120 and an oxygen concentrator 130. As shown, an output 131 of oxygen concentrator 130 is fluidly coupled to an inlet 121 of respiratory ventilation device 120, so that respiratory ventilation device 120 provides oxygen-enriched inhalation gas 123 to patient 101 during ventilation therapy.

Respiratory ventilation device 120 may be any technically feasible respiratory ventilator capable of moving breathable air into the lungs of patient 101. Thus, respiratory ventilation device 120 facilitates the breathing of patient 101, who may be physically unable to breathe, or may be breathing insufficiently. Inhalation gas 123 may be delivered from respiratory ventilation device 120 to patient 101 by a nasal mask, nasal cannula, intubation, or the like.

In some embodiments, respiratory ventilation device 120 is configured to employ entrainment of ambient air in the delivery of inhalation gas 123 to patient 101. In such embodiments, respiratory ventilation device 120 directly provides a source gas 122 that is only a portion of the inhalation gas 123 inhaled by patient 101. The remaining portion of inhalation gas 123 is ambient air 124, which has been entrained by source gas 122. In general, source gas 122 is typically a relatively small portion of inhalation gas 123, for example between about 10% to 50% of inhalation gas 123. Thus, when the instantaneous flow rate requirement for respiratory ventilation device 120 during an inhalation by patient 101 is, for example, 100 LPM, the instantaneous flow rate requirement for inhalation gas 123 is also 100 LPM, while the instantaneous flow rate requirement for source gas 122 is only about 10 to 30 LPM. In such embodiments, most or all of source gas 122 may be provided by oxygen concentrator 130 as an oxygen-enriched product gas 132. Alternatively, source gas 122 may include a combination of oxygen-enriched product gas 132 and ambient air that s mixed with oxygen-enriched product gas 132.

Oxygen concentrator 130 is configured to produce an oxygen-enriched product gas for providing oxygen therapy to patient 101. Thus, patient 101 receives both ventilation therapy via respiratory ventilation device 120 and oxygen therapy. Oxygen concentrator 130 may be any technically feasible oxygen concentrator suitable for providing oxygen-enriched product gas 132 to respiratory ventilation device 120 at a sufficient volume and having a minimum required oxygen concentration. For example, oxygen concentrator 130 may be configured to employ a pressure swing adsorption (PSA) process, a rapid pressure swing adsorption (RPSA) process, a vacuum pressure swing adsorption (VPSA), or any other derivative process thereof.

In some embodiments, oxygen concentrator 130 is configured as a conventional semi-portable (wheeled) or non-portable (stationary) oxygen concentrator, for example for use in a home or hospital setting. In other embodiments, oxygen concentrator 130 is a portable oxygen concentrator, such as a device configured to be carried in a backpack. In such embodiments, respiratory ventilation device 120 may also be configured as a portable or ultra-portable device.

Figure 2:
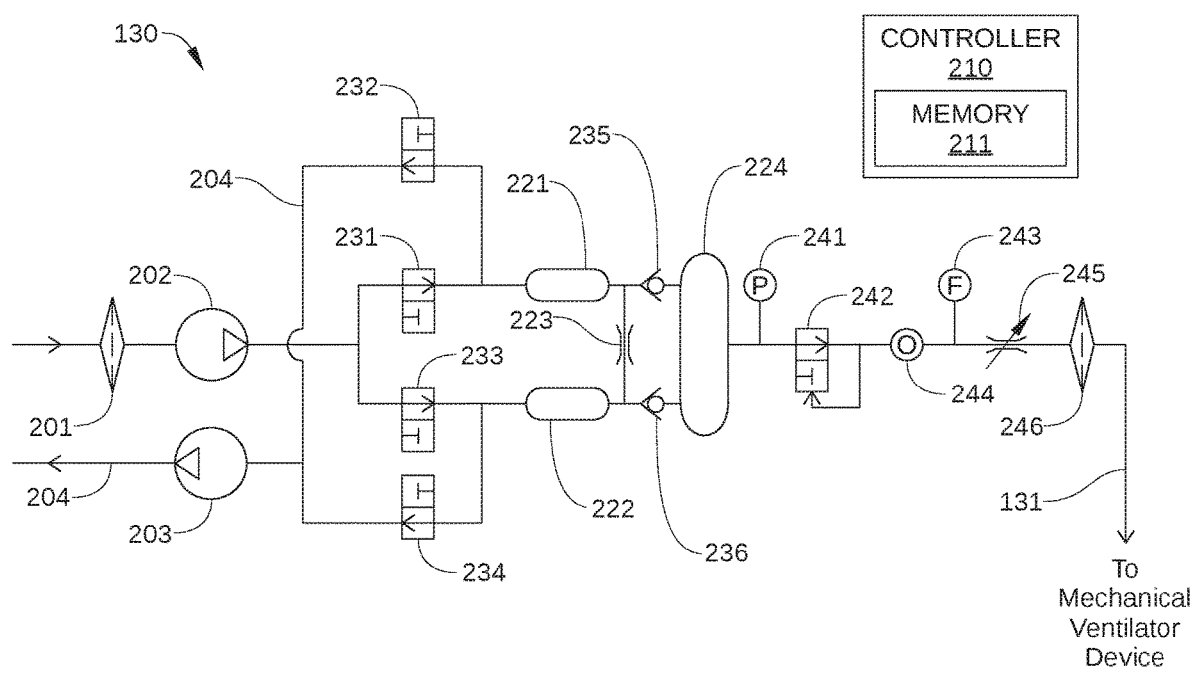
FIG. 2 is a more detailed schematic illustration of the oxygen concentrator of FIG. 1, according to various embodiments of the present invention.

FIG. 2 is a more detailed schematic illustration of oxygen concentrator 130, according to various embodiments of the present invention. As noted above, oxygen concentrator 130 is configured to produce an oxygen-enriched product gas for providing oxygen therapy to a patient who is also receiving ventilation therapy via respiratory ventilation device 120. As such, oxygen concentrator 130 includes, without limitation, an inlet filter 201, a pump 202, and, in some embodiments, a vacuum pump 203, all connected via pneumatic plumbing 204, as shown in FIG. 2.

Oxygen concentrator 130 also includes a first sieve bed 221 and a second sieve bed 222, fluidly connected to each other by an equalization orifice 223, and a product tank 224 that is fluidly connected to first sieve bed 221 and second sieve bed 222. First sieve bed 221 and second sieve bed 222 are each configured to remove nitrogen from air present therein, so that product gas exiting first sieve bed 221 or second sieve bed 222 is an oxygen-enriched gas, Typically, first sieve bed 221 and second sieve bed 222 each include a nitrogen-adsorbing material, such as a nitrogen-adsorbing zeolite. Consequently, as air flows into one of first sieve bed 221 or second sieve bed 222, the air passes through the nitrogen-adsorbing material, a significant portion of the nitrogen is adsorbed, and the remaining gas in the sieve bed is primarily oxygen. This oxygen-enriched gas can then flow into product tank 224.

Oxygen concentrator 130 further includes a first sieve bed fill valve 231 coupled to an inlet of first sieve bed 221, a first sieve bed dump valve 232 fluidly coupled to an outlet of first sieve bed 221, a second sieve bed fill valve 233 coupled to an inlet of second sieve bed 222, and a second sieve bed dump valve 234 fluidly coupled to an outlet of second sieve bed 222. First sieve bed fill valve 231 is a controllable valve that selectively allows entry of air or any other suitable gas to enter first sieve bed 221. First sieve bed dump valve 232 is a controllable valve that selectively allows gas present in first sieve bed 221 to exit first sieve bed 221 when at a higher pressure than ambient. Second sieve bed fill valve 233 and second sieve bed dump valve 234 operate similarly with respect to second sieve bed 222.

Oxygen concentrator 130 also includes a first check valve 235 disposed between first sieve bed 221 and product tank 224 that is configured to prevent flow or pressure from exiting product tank 224 and entering first sieve bed 221. Similarly, oxygen concentrator 130 includes a second check valve 236 disposed between second sieve bed 222 and product tank 224 that is configured to prevent flow or pressure from exiting product tank 224 and entering second sieve bed 222.

Oxygen concentrator 130 further includes a controller 210 that is coupled to one or more of first sieve bed fill valve 231, first sieve bed dump valve 232, second sieve bed fill valve 233, second sieve bed dump valve 234, and any sensors (described below) included in oxygen concentrator 130. Controller 210 may be any suitable processor implemented as a central processing unit (CPU), an application-specific integrated circuit (ASIC), a field programmable gate array (FPGA), any other type of processing unit, or a combination of different processing units. In general, controller 210 may be any technically feasible hardware unit capable of processing input signals or other data and/or executing software applications to facilitate operation of oxygen concentrator 130 as described herein. Furthermore, in some embodiments, controller 210 may include a memory 211. Memory 211 may include volatile memory, such as a random access memory (RAM) module, and non-volatile memory, such as a flash memory unit, a read-only memory (ROM), or any other type of memory unit or combination thereof suitable for use in controller 210. In such embodiments, memory 211 is configured to store any instructions, software programs, operating system, drivers, and the like, that facilitate operation of controller 210 and any processors making up controller 210.

In some embodiments, oxygen concentrator 130 further includes one or more of a tank pressure measurement device 241, a pressure regulator 242, a flow measurement device 243, an oxygen sensor 244, a manual flow-control device 245, such as an adjustable orifice, and an outlet filter 246, each disposed downstream of product tank 224 as shown or in any suitable configuration.

In operation, oxygen concentrator 130 generates oxygen-enriched product gas 132 via a process that includes a fill phase for each of first sieve bed 221 and second sieve bed 222, a dump phase for each of first sieve bed 221 and second sieve bed 222, and an equalization phase. The fill phase for first sieve bed 221 occurs concurrently with the dump phase for second sieve bed 222, while the fill phase for second sieve bed 222 occurs concurrently with the dump phase for first sieve bed 221. By contrast, the equalization phase for first sieve bed 221 and the equalization phase for second sieve bed 221 occur simultaneously.

Figure 3:
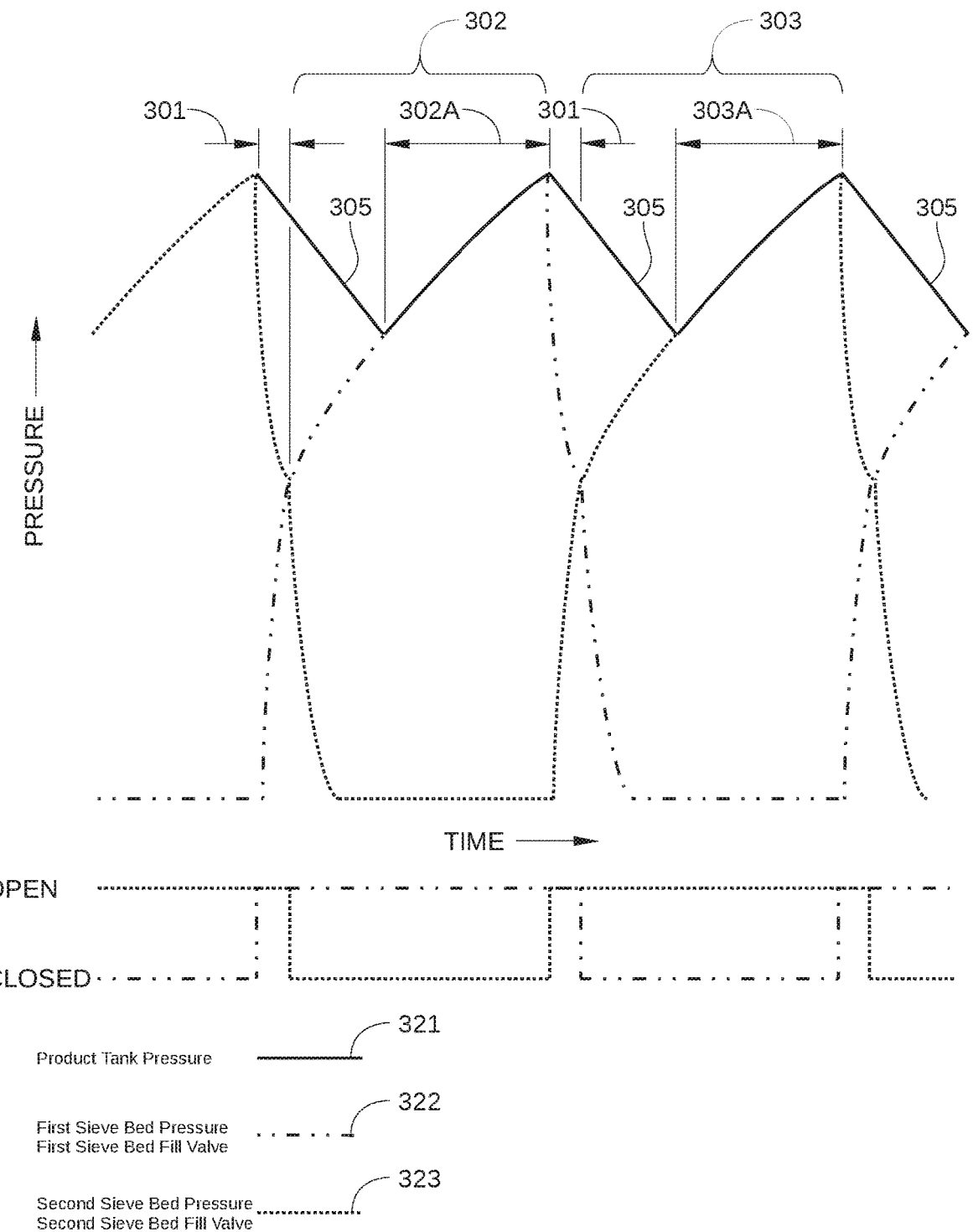
FIG. 3 is a graph illustrating pressure at various locations within the oxygen concentrator of FIG. 2 as the oxygen-ventilation system provides a constant flow of an oxygen-enriched gas, according to various embodiments of the invention.

FIG. 3 is a graph illustrating pressure at various locations within oxygen concentrator 130 as oxygen concentrator 130 delivers a constant flow of an oxygen-enriched gas, according to various embodiments of the invention. The process by which oxygen concentrator 130 provides the oxygen-enriched gas includes an equalization phase 301, a first dump/fill phase 302, and a second dump/fill phase 303. A product tank pressure 321, a first sieve bed pressure 322, and a second sieve bed pressure 323 are all depicted over the course of equalization phase 301, first dump/fill phase 302, and second dump/fill phase 303. In addition, actuation of first sieve bed fill valve 231 and second sieve bed fill valve 233 is shown. For clarity, actuation of first sieve bed dump valve 232 and second sieve bed dump valve 234 is omitted from FIG. 3. Also depicted in FIG. 3 are a first fill time 302A, in which product tank 224 is filled from first sieve bed 221, and a second fill time 303A, in which product tank 224 is filled from second sieve bed 222. It is noted that the filling phase for first sieve bed 221 and the dump phase for second sieve bed 222 take place during first dump/fill phase 302, while the fill phase for second sieve bed 222 and the dump phase for first sieve bed 221 take place during second dump/fill phase 303.

In the filling phase for first sieve bed 221 (i.e., first dump/fill phase 302), the output of pump 202, which is controlled by first sieve bed fill valve 231 and second sieve bed fill valve 233, is directed to first sieve bed 221, in which nitrogen is removed and an oxygen-enriched gas is formed. As a result, the pressure in first sieve bed 221 increases as shown. When pressure in first sieve bed 221 increases to a level equal to the pressure in product tank 224, first fill time 302A begins. That is, first sieve bed pressure 322 is equal to product tank pressure 321, the corresponding check valve (i.e., first check valve 235) opens, the oxygen-enriched gas in first sieve bed 221 enters product tank 224, and the pressure in product tank 224 increases in parallel with and equal to the pressure in first sieve bed 221, as shown.

The dump phase for second sieve bed 222 also occurs during first dump/fill phase 302 (and concurrent with the above-described filling phase for first sieve bed 221). In the dump phase for second sieve bed 222, second sieve bed dump valve 234 is open to ambient, so that accumulated nitrogen within second sieve bed 222 is dumped and the pressure in second sieve bed decreases as shown.

It is noted that, as pump 202 fills first sieve bed 221 and the pressure therein exceeds the pressure in second sieve bed 222, a portion of the oxygen-enriched gas formed in first sieve bed 221 flows into second sieve bed 222 via equalization orifice 223. As a result, the removal of nitrogen from the second sieve bed 222, which is in the dump phase, is facilitated. It is further noted that the rate at which the pressure of first sieve bed 221 increases is a function of multiple factors, including: the pump flow characteristics of pump 202; the volume of first sieve bed 221; the size of equalization orifice 223, and, once the pressure in first sieve bed 221 equals the pressure in product tank 224, the volume of product tank 224.

After the currently filling sieve bed, i.e., first sieve bed 221, is saturated with nitrogen or is approaching saturation, equalization phase 301 is performed, i.e., the equalization phase 301 that occurs between first dump/fill phase 302 and second dump/fill phase 303. Equalization phase 301 begins when first sieve bed fill valve 231 and second sieve bed fill valve 233 open, while first sieve bed dump valve 232 and second sieve bed dump valve 234 close. As a result, pressure in first sieve bed 221 and second sieve bed 222 equalizes via equalization orifice 223, so that the pressure in what was the filling sieve bed (i.e., first sieve bed 221) is used to quickly increase pressure in what was the non-filling sieve bed (i.e., second sieve bed 222). During this equalization step 301, first sieve bed 221 and second sieve bed 222 both receive air from pump 202 without an exhausting of gases, resulting in relatively rapid pressure increase in each sieve bed.

Upon completion of equalization phase 301, second dump/fill phase 303 begins, in which first sieve bed 221 is exhausted to ambient via first sieve bed dump valve 232, and second sieve bed 222 is filled via second sieve bed fill valve 233. The above-described process then repeats and alternates between first sieve bed 221 and second sieve bed 222 to cyclically charge product tank 224 with an oxygen-enriched gas, such as oxygen-enriched product gas 132 in FIG. 1.

FIG. 3 depicts the pressure waveforms of first sieve bed 221, second sieve bed 222, and product tank 224 when oxygen concentrator 130 supplies a constant flow of oxygen-enriched gas via a typical PSA oxygen concentrator process. The saw tooth profile of product tank pressure 321 shows the increase of pressure of filling from one of first sieve bed 221 and second sieve bed 222, and the subsequent linear reduction in pressure during draining due to the constant flow delivery of the oxygen-enriched gas from product tank 224. The rate of decay (slope) 305 in product tank pressure 321 when not filling is a function of the volume of product tank 224 and the flow rate at which the oxygen-enriched gas is delivered from product tank 224. For example, when such a flow rate is reduced, the slope 305 becomes less negative.

It is noted that the increase in product tank pressure 321 continues until a dump/fill phase ends, and the time duration of each dump/fill phase is generally set as a predetermined cycle time. Further, in some embodiments, controller 210 is configured to adjust the min-to-max range of product tank pressure 321 during operation for a particular product flow rate (i.e., slope 305) by adjusting a control output in oxygen concentrator 130 to modify operation of oxygen concentrator 130. For example, controller 210 may adjust the timing of one or more valves in oxygen concentrator 130, or may adjust an output of pump 202 in oxygen concentrator 130.

In embodiments in which controller 210 adjusts the timing of one or more valves in oxygen concentrator 130, controller 210 can increase or decrease the duration of equalization phase 301 and/or each dump/fill phase. In this way, controller 210 increases or decreases the maximum product tank pressure and/or minimum product tank pressure achieved during steady state operation. For example, increasing the duration of each dump/fill phase allows more time for each sieve bed to charge product tank 224. As a result, product tank pressure 321 reaches a higher pressure and contains more oxygen-enriched gas before the next equalization phase 301 begins. Conversely, controller 210 decreasing the duration of each dump/fill phase has an opposite effect.

In embodiments in which controller 210 adjusts the output of pump 202, controller 210 can increase or decrease the quantity of gas flowing into each sieve bed during the fill phase, thereby increasing or decreasing the maximum product tank pressure and/or minimum product tank pressure achieved during steady state operation. For example, increasing the output of pump 202 during each dump/fill phase allows more gas to flow into product tank 224. As a result, product tank pressure 321 reaches a higher pressure and contains more oxygen-enriched gas before the next equalization phase 301 begins. Conversely, decreasing the output of pump 202 during each dump/fill phase has an opposite effect.

According to embodiments of the invention, the output of oxygen concentrator 130, as shown in FIG. 1, is fluidly connected to respiratory ventilation device 120, which does not provide a constant flow of inhalation gas 123. Instead, respiratory ventilation device 120 provides inhalation gas 123 to patient 101 intermittently, typically in response to an inspiratory effort by patient 101. As a result, oxygen-enriched product gas 132 is delivered from product tank 224 of oxygen concentrator 130 in intermittent pulses, rather than at a constant flow rate. Consequently, the pressure waveforms of first sieve bed 221, second sieve bed 222, and product tank 224 of oxygen concentrator 130 behave differently than depicted in FIG. 3. Such behavior is illustrated in FIG. 4.

Figure 4:
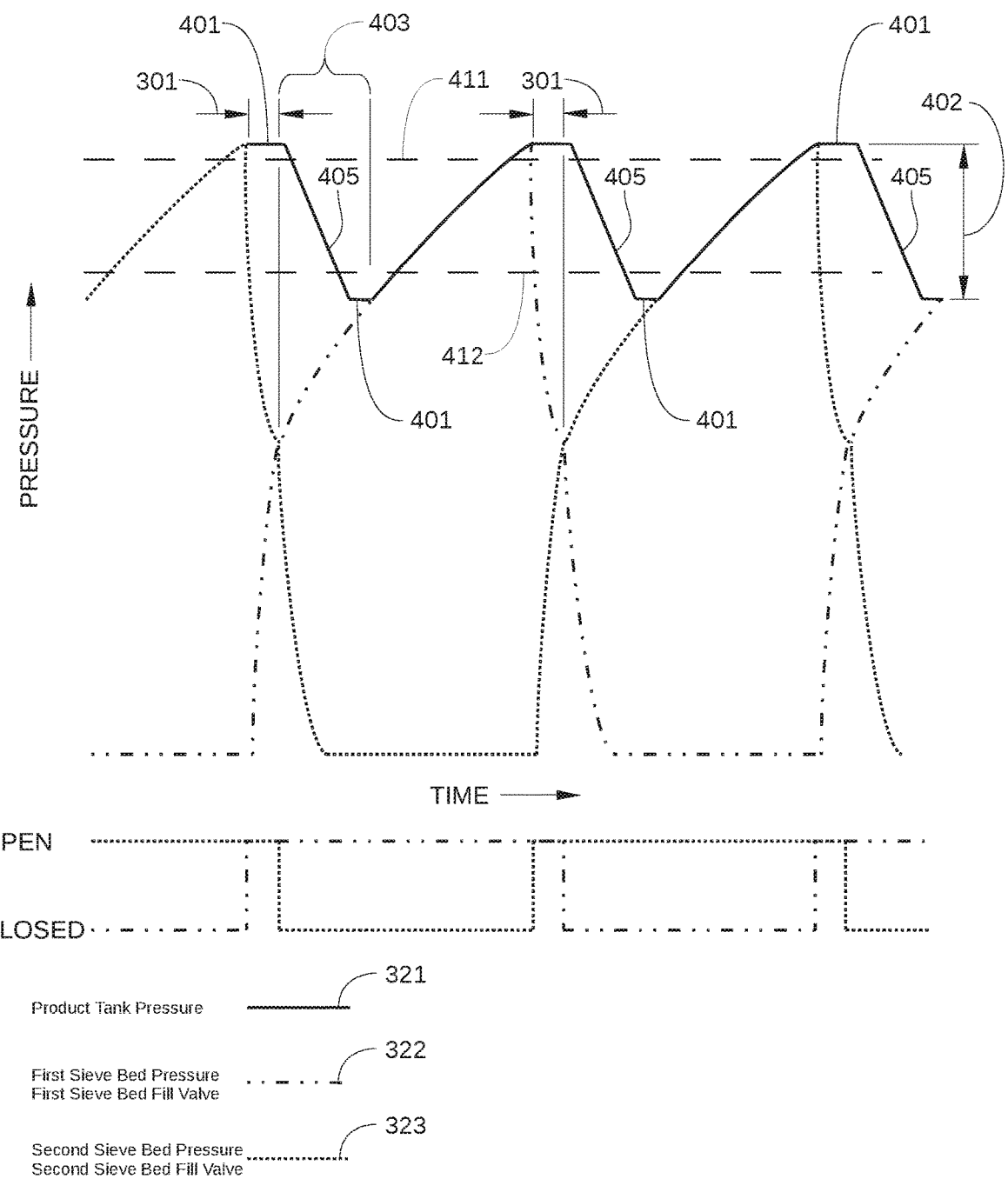
FIG. 4 is a graph illustrating pressure at various locations within the oxygen concentrator of FIG. 2 as the oxygen-ventilation system provides an intermittent volume or bolus of an oxygen-enriched gas, according to various embodiments of the invention.

FIG. 4 is a graph illustrating pressure at various locations within oxygen concentrator 130 as oxygen concentrator 130 provides an intermittent volume of oxygen-enriched gas to respiratory ventilation device 120, according to various embodiments of the invention. The process by which oxygen concentrator 130 provides the oxygen-enriched gas is substantially similar to that for delivering a constant flow, and includes equalization phase 301, first dump/fill phase 302, and second dump/fill phase 303. However, as shown in FIG. 4, in a spontaneous delivery scenario, the pressure waveform behavior of product tank pressure 321 can be significantly different than in the constant flow delivery scenario illustrated in FIG. 3. In a spontaneous delivery scenario, respiratory ventilation device 130 spontaneously and intermittently delivers inhalation gas 123, which includes oxygen-enriched gas 132 from product tank 224 of oxygen concentrator 120. In such a spontaneous delivery scenario, significant characteristics of the pressure waveform behavior of product tank 224 include constant pressure intervals 401 and pressure drops 402.

Constant pressure intervals 401, i.e., the horizontal segments of product tank pressure 321, indicate that respiratory ventilation device 130 is not delivering inhalation gas 123 to patient 101 at a time that a sieve bed is not delivering oxygen-enriched gas to product tank 224. That is, the presence of a constant pressure interval 401 indicates that respiratory ventilation device 130 is not delivering inhalation gas 123 to patient 101 either during equilibrium phase 301 or during a portion 403 of a fill phase in which product tank pressure 321 is greater than first sieve bed pressure 322 or second sieve bed pressure 323. By contrast, slopes 405 result when respiratory ventilation device 130 spontaneously delivers inhalation gas 123. Slope 405 is a function of the flow rate of oxygen-enriched gas 132 from oxygen concentrator 130, to ventilation device 103 and the volume of product tank 224. Furthermore, the magnitude of pressure drop 402 (which occurs during a time that a sieve bed is not delivering oxygen-enriched gas to product tank 224) is a function of the quantity of oxygen-enriched gas delivered from oxygen concentrator 130, and the volume of product tank 224.

Therefore, in light of the above, the pressure waveform of product tank pressure 321, specifically constant pressure intervals 401 and pressure drops 402, can indicate useful patient status information. For example, by monitoring product tank pressure via tank pressure measurement device 241 or any other suitable device, controller 210 can determine when and how frequently patient 101 is inhaling, the intermittent flow rate of oxygen-enriched gas the volume of oxygen-enriched gas 132 that is inhaled by patient 101 in each breath, the average flow rate (or minute volume) of oxygen-enriched gas 132 consumed by patient 101, and the like.

Furthermore, based on the pressure waveform of product tank pressure 321, in some embodiments controller 210 is configured to adjust the min-to-max range of product tank pressure 321 during operation based on the pressure waveform of product tank pressure 321 and/or a measured output flow rate of oxygen-enriched gas 132. In such embodiments, controller 210 adjusts a control output in oxygen concentrator 130, such as the timing of one or more valves in oxygen concentrator 130, or an output of pump 202 in oxygen concentrator 130. In one such embodiment, in response to determining that oxygen concentrator 130 does not meet or exceed a supply gas requirement, controller 210 may make such an adjustment.

For example, controller 210 may determine that product tank pressure 321 in product tank 224 is greater than a maximum target tank pressure 411 or less than a minimum target tank pressure 412. In such an embodiment, controller 210 typically makes such a determination during a time interval between patient inhalations. In such embodiments, adjusting the timing of one or more valves in oxygen concentrator 130 and/or adjusting an output of pump 202 can increase or decrease the duration of equalization phase 301 and/or each dump/fill phase. In this way, controller 210 increases or decreases the maximum product tank pressure and/or minimum product tank pressure achieved during operation, as described above in conjunction with FIG. 3. Thus, as the oxygen and ventilation therapy requirements of patient 101 change over time, controller 210 can detect when oxygen concentrator 130 fails to meet a supply gas requirement, and modify operation of oxygen concentrator 130 accordingly.

In another example, controller 210 is configured to determine that a flow rate of oxygen-enriched gas from product tank 224 is greater than a maximum target flow rate or less than a minimum target flow rate. In such embodiments, controller 210 makes such a determination based on an output flow rate measured during a patient inhalation by flow measurement device 243. In such embodiments, when the measured flow rate is less than the minimum target flow rate, controller 210 can adjust a control output to increase the maximum product tank pressure achieved during each fill/dump cycle. For example, controller 210 may increase an output of pump 202 and/or increase the duration of each fill/dump cycle. Conversely, when the measured flow rate is greater than the maximum target flow rate, controller 210 can adjust a control output to decrease the maximum product tank pressure achieved during each fill/dump cycle, and/or reduce an output pressure of pressure regulator 242. For example, controller 210 may decrease an output of pump 202 or decrease the duration of each fill/dump cycle.

In another example, controller 210 is configured to determine that an oxygen concentration of oxygen-enriched gas from product tank 224 is less than a minimum target value. In such embodiments, controller 210 makes such a determination based on an oxygen concentration measurement performed during a patient inhalation by oxygen sensor 244. In such embodiments, when the measured oxygen concentration is less than the minimum target concentration, controller 210 can adjust a control output to increase the maximum product tank pressure achieved during each fill/dump cycle. In this way, more oxygen-enriched gas is delivered to product tank 224, and product tank 224 is less likely to be over-utilized and have a lower concentration of oxygen in oxygen-enriched gas 132.

In some embodiments, controller 210 is configured to determine when or if oxygen concentrator 130 is fluidly coupled to respiratory ventilation device 120, based on the detection of constant pressure intervals 401. Alternatively or additionally, controller 210 may be configured to determine that oxygen concentrator 130 is fluidly coupled to respiratory ventilation device 120 based on the variability of pressure drops 402. Such variability can indicate that oxygen-enriched gas 132 is being delivered based on a spontaneous respiration rate of patient 101.

In some embodiments, flow measurement device 243 may be employed in addition to or in lieu of tank pressure measurement device 241 to determine that oxygen concentrator 130 is fluidly coupled to respiratory ventilation device 120. In such embodiments, the difference in outlet flow delivery for a constant flow scenario is readily discernible from the intermittent flow evident in a spontaneous delivery scenario, i.e., when oxygen concentrator 130 is fluidly coupled to respiratory ventilation device 120 while respiratory ventilation device 120 spontaneously delivers oxygen-enriched gas 132 to patient 101.

In some embodiments, controller 210 is configured to adjust an output of one or more sensors in oxygen concentrator 130 with a correction factor when controller 210 determines that oxygen concentrator 130 is fluidly coupled to respiratory ventilation device 120. Some sensor technologies may be sensitive to system pressure, such as oxygen sensor 244 and flow measurement device 243. Thus, in situations in which fluidly connecting oxygen concentrator 130 to a respiratory ventilation device 120 causes portions of oxygen concentrator 130 to operate under elevated system pressure, controller 210 can compensate for sensor variation due to such elevated system pressure. For example, a pressure-based correction factor may be applied to the output of any affected sensor.

Figure 5:
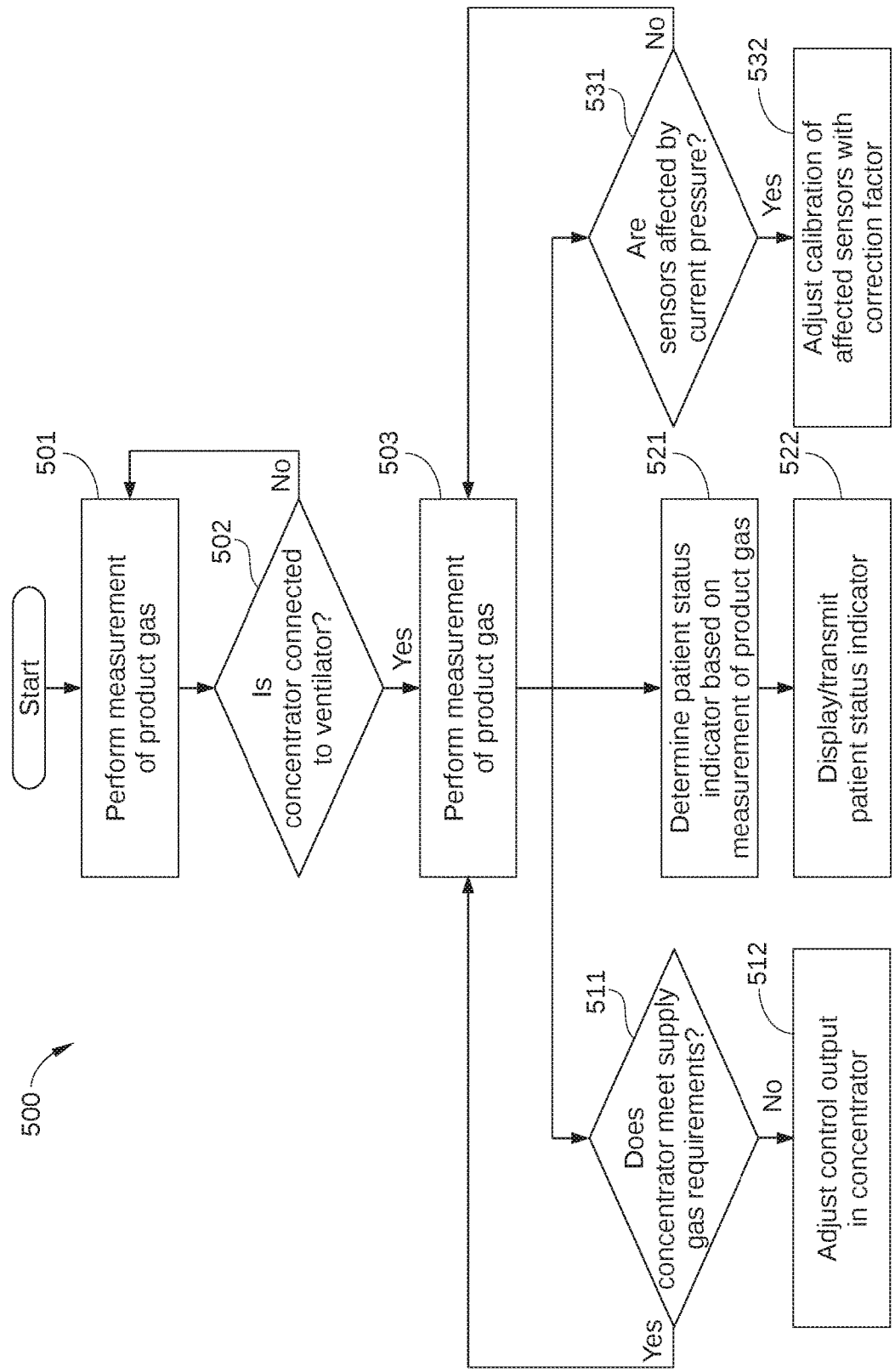
FIG. 5 sets forth a flowchart of method steps for operating an oxygen concentrator, according to various embodiments of the present invention.

FIG. 5 sets forth a flowchart of method steps for operating an oxygen concentrator, according to various embodiments of the present invention. Although the method steps are described with respect to the systems of FIGS. 1-4, persons skilled in the art will understand that any system configured to perform the method steps, in any order, falls within the scope of the present disclosure.

As shown, a method 500 begins at step 501, in which controller 210 performs a measurement of a product gas of oxygen concentrator 130, such as oxygen-enriched gas 132. In some embodiments, the measurement of the product gas includes measuring product tank pressure 321 of product tank 224, measuring an output flow rate of the product gas with flow measurement device 243, or a combination of both. In some embodiments, a plurality of such measurements are made over time by controller 210 and the appropriate sensors, so that a pressure waveform or flow rate waveform can be constructed.

In step 502, controller 210 determines whether an output of oxygen concentrator 130 is fluidly coupled to respiratory ventilation device 120. For example, in some embodiments controller 210 makes such a determination based on a pressure waveform of product tank 224, a flow rate waveform constructed with measurements made by flow measurement device 243, or a combination of both. As described above in conjunction with FIGS. 3 and 4, pressure and flow rate waveforms can readily indicate that the output of oxygen concentrator 130 is fluidly connected to a device that utilizes oxygen-enriched gas 134 in intermittent, spontaneous bursts, such as respiratory ventilation device 120. If no, method 500 proceeds back to step 501; if no, method 500 proceeds to step 503.

In step 503, controller 210 performs a measurement of a product gas of oxygen concentrator 130. In some embodiments, the measurement of the product gas includes measuring product tank pressure 321 of product tank 224, measuring an output flow rate of a product gas, such as a stream of oxygen-enriched gas 134 with flow measurement device 243, or a combination of both.

In step 511, controller 210 determines whether oxygen concentrator 130 meets one or more supply gas requirements. In some embodiments, the supply gas requirement is a minimum and/or maximum flowrate of oxygen-enriched gas 132 from oxygen concentrator 130 during an inhalation by patient 101. In some embodiments, the supply gas requirement is a minimum and/or maximum product tank pressure. In some embodiments, the supply gas requirement is a minimum and/or maximum oxygen concentration of oxygen-enriched gas 132. If yes, method 500 proceeds back to step 503; if no, method 500 proceeds to step 512.

In step 512, controller 210 adjusts a control output in concentrator 130, such as the timing of one or more valves in oxygen concentrator 130, or an output of pump 202 in oxygen concentrator 130. As described above, the control output is adjusted to increase or decrease product tank pressure 321 in product tank 224 and/or increase or decrease a supply gas flow rate.

In step 521, controller 210 determines one or more patient status indicators based on one or more measurements performed in step 503. For example, based on the pressure waveform of product tank pressure 321, controller 210 can determine patient respiration rate, intermittent flow rate, minute volume of oxygen-enriched gas 134 consumed by patient 101, and the like. In some embodiments, controller 210 determines a current therapy mode. For example, possible therapy modes detectable by pressure waveforms and flow rate waveforms, as described herein, include: volume ventilation (VV), in which a preset volume is delivered to patient 101; pressure ventilation (PV) or pressure control ventilation (PCV), in which a preset pressure is delivered to patient 101; and pressure regulated volume control (PRVC), in which pressure ventilation is delivered such that the pressure is automatically adjusted by the ventilator to provide a set tidal volume, among others.

In step 522, controller 210 causes the patient status determined in step 521 to be displayed and/or transmitted for storage and display. In some embodiments, alarms associated with the various patient status indicators are also transmitted and/or displayed.

In step 531, controller 210 determines whether any of the sensors included in oxygen concentrator 130 are affected by the currently measured pressure in oxygen concentrator 210. For example, above certain system pressures, measurement accuracy of flow measurement device 243 and/or oxygen sensor 244 may be affected. If no, method 500 proceeds back to step 503; if yes, method 500 proceeds to step 532.

In step 532, controller 210 adjusts the output of any affected sensors, as determined in step 531. For example, in some embodiments, controller 210 applies a suitable correction factor to the output of an affected sensor. In such embodiments, the correction factor typically varies as a function of the current system pressure in oxygen controller 130, such as a pressure in the portion of pneumatic plumbing 204 fluidly coupled to the affected sensors. Furthermore, in such embodiments, the correction factor may be selected from a look-up table included in controller 210 or memory 211.

In sum, the output of an oxygen concentrator is fluidly connected to a respiratory ventilation device. Furthermore, a controller of the oxygen concentrator is configured to detect the fluid connection to the respiratory ventilation device, and to adjust operation of the oxygen concentrator accordingly when the product gas of the oxygen concentrator does not meet a supply gas requirement of the respiratory ventilation device. In some embodiments, the controller is also configured to monitor one or more aspects of patient status.

At least one advantage of the disclosed techniques is that an oxygen concentrator can be effectively connected to a mechanical ventilator without the performance of the oxygen concentrator being deleteriously affected. Consequently, the use of combined oxygen therapy and ventilation therapy is greatly facilitated. An additional advantage is that certain aspects of patient status can be monitored noninvasively as part of the normal operation of the oxygen concentrator.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method, or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Aspects of the present disclosure are described above with reference to flowchart illustrations and/or block diagrams of methods, apparatus (systems) and computer program products according to various embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The invention has been described above with reference to specific embodiments. Persons of ordinary skill in the art, however, will understand that various modifications and changes may be made thereto without departing from the broader spirit and scope of the invention as set forth in the appended claims. For example, and without limitation, although many of the descriptions herein refer to devices, persons skilled in the art will appreciate that the systems and techniques described herein are applicable to other types of devices. The foregoing description and drawings are, accordingly, to be regarded in an illustrative rather than a restrictive sense.

What is claimed is:

1. A method for operating an oxygen concentrator, the method comprising:
   measuring a product gas within an oxygen concentrator over time to produce a product gas measurement waveform;
   determining that an output of the oxygen concentrator is fluidly connected to a ventilator by detecting one or more constant pressure intervals and one or more pressure drop intervals within the product gas measurement waveform;
   in response to determining that the oxygen concentrator is fluidly connected to the ventilator, determining that the output of the oxygen concentrator does not meet a supply gas requirement of the ventilator based on the product gas measurement waveform; and
   in response to determining that the output of the oxygen concentrator does not meet the supply gas requirement, adjusting a control output in the oxygen concentrator to modify operation of the oxygen concentrator.

2. The method of claim 1, wherein measuring the product gas comprises at least one of measuring a pressure in a tank storing an oxygen-enriched gas or measuring an output flow rate of an oxygen-enriched gas stream.

3. The method of claim 2, wherein determining that the output of the oxygen concentrator does not meet the supply gas requirement of the ventilator comprises determining that the pressure in the tank during a time interval between patient inhalations is greater than a maximum target tank pressure or less than a minimum target tank pressure.

4. The method of claim 2, wherein determining that the output of the oxygen concentrator does not meet the supply gas requirement of the ventilator comprises determining that the output flow rate of the oxygen-enriched gas stream during a patient inhalation is greater than a maximum target flow rate or less than a minimum target flow rate.

5. The method of claim 2, wherein adjusting the control output in the oxygen concentrator comprises adjusting a timing of one or more valves in the oxygen concentrator to change a fill time of a sieve bed within the oxygen concentrator.

6. The method of claim 2, wherein adjusting the control output in the oxygen concentrator comprises adjusting an output of a gas compressor within the oxygen concentrator.

7. The method of claim 1, further comprising determining at least one of a patient breath rate, a delivered volume of an oxygen-enriched gas stream, and a patient therapy mode associated with the ventilator based on the product gas measurement waveform.

8. The method of claim 1, further comprising adjusting an output of a sensor within the oxygen concentrator with a correction factor to correct for the oxygen concentrator being fluidly connected to the ventilator.

9. One or more non-transitory computer-readable storage media including instructions that, when executed by one or more processors, cause the one or more processors to perform the steps of:
   measuring a product gas within an oxygen concentrator over time to produce a product gas measurement waveform;
   determining that an output of the oxygen concentrator is fluidly connected to a ventilator by detecting one or more constant pressure intervals and one or more pressure drop intervals within the product gas measurement waveform;
   in response to determining that the oxygen concentrator is fluidly connected to the ventilator, determining that the output of the oxygen concentrator does not meet a supply gas requirement of the ventilator based on the product gas measurement waveform; and
   in response to determining that the output of the oxygen concentrator does not meet the supply gas requirement, adjusting a control output in the oxygen concentrator to modify operation of the oxygen concentrator.

10. The one or more non-transitory computer-readable storage media of claim 9, wherein measuring the product gas comprises at least one of measuring a pressure in a tank storing an oxygen-enriched gas or measuring an output flow rate of an oxygen-enriched gas stream.

11. The one or more non-transitory computer-readable storage media of claim 10, wherein determining that the output of the oxygen concentrator does not meet the supply gas requirement of the ventilator comprises determining that the pressure in the tank during a time interval between patient inhalations is greater than a maximum target tank pressure or less than a minimum target tank pressure.

12. The one or more non-transitory computer-readable storage media of claim 10, wherein determining that the output of the oxygen concentrator does not meet the supply gas requirement of the ventilator comprises determining that the output flow rate of the oxygen-enriched gas stream during a patient inhalation is greater than a maximum target flow rate or less than a minimum target flow rate.

13. The one or more non-transitory computer-readable storage media of claim 10, wherein adjusting the control output in the oxygen concentrator comprises adjusting a timing of one or more valves in the oxygen concentrator to change a fill time of a sieve bed within the oxygen concentrator.

14. The one or more non-transitory computer-readable storage media of claim 9, further comprising determining at least one of a patient breath rate, a delivered volume of an oxygen-enriched gas stream, or a patient therapy mode associated with the ventilator based on the product gas measurement waveform.

15. The one or more non-transitory computer-readable storage media of claim 9, further comprising adjusting an output of a sensor within the oxygen concentrator with a correction factor to correct for the oxygen concentrator being fluidly connected to the ventilator.

16. The one or more non-transitory computer-readable storage media of claim 15, wherein the sensor comprises at least one of an oxygen sensor or a flow rate sensor.

17. A system, comprising:
a ventilator;
an oxygen concentrator with an outlet fluidly coupled to an inlet of the ventilator; and
a controller configured to:
  receive a measurement of a product gas within the oxygen concentrator over time to produce a product gas measurement waveform;
  determine that an output of the oxygen concentrator is fluidly connected to the ventilator by detecting one or more constant pressure intervals and one or more pressure drop intervals within the product gas measurement waveform;
  in response to determining that the oxygen concentrator is fluidly connected to the ventilator, determine that the output of the oxygen concentrator does not meet a supply gas requirement of the ventilator based on the product gas measurement waveform; and
  in response to determining that the output of the oxygen concentrator does not meet the supply gas requirement, adjust a control output in the oxygen concentrator to modify operation of the oxygen concentrator.

18. The system of claim 17, further comprising adjusting an output of a sensor within the oxygen concentrator with a correction factor to correct for the oxygen concentrator being fluidly connected to the ventilator.

19. The system of claim 18, wherein the sensor comprises at least one of an oxygen sensor or a flow rate sensor.

20. The system of claim 17, wherein the product gas is measured by at least one of measuring a pressure in a tank storing an oxygen-enriched gas or measuring an output flow rate of an oxygen-enriched gas stream.

21. A system, comprising:
a ventilator;
an oxygen concentrator with an outlet fluidly coupled to an inlet of the ventilator; and
a controller configured to:
  receive a measurement of a product gas within the oxygen concentrator to produce a product gas measurement waveform;
  detect one or more constant pressure intervals and one or more pressure drop intervals within the product gas measurement waveform;
  determine that the output of the oxygen concentrator does not meet a supply gas requirement of the ventilator based on the product gas measurement waveform; and
  in response to determining that the output of the oxygen concentrator does not meet the supply gas requirement, adjust a control output in the oxygen concentrator to modify operation of the oxygen concentrator.

22. The system of claim 21, further comprising determining at least one of a patient breath rate, a delivered volume of an oxygen-enriched gas stream, or a patient therapy mode associated with the ventilator based on the product gas measurement waveform.

23. The system of claim 21, further comprising adjusting an output of a sensor within the oxygen concentrator with a correction factor to correct for the oxygen concentrator being fluidly connected to the ventilator.

* * * * *